United States Patent [19]

Sano et al.

[11] Patent Number: 5,415,840
[45] Date of Patent: May 16, 1995

[54] LIQUID SAMPLE AUTOMATIC ANALYZER

[75] Inventors: Kazuhiro Sano, Ibaraki; Susumu Kai; Shigeru Yonekawa, both of Katsuta, all of Japan

[73] Assignee: Hitachi, Ltd., Tokyo, Japan

[21] Appl. No.: 138,353

[22] Filed: Oct. 18, 1993

[30] Foreign Application Priority Data

Oct. 19, 1992 [JP] Japan .................... 4-279865

[51] Int. Cl.[6] .............. G01N 35/02; G01N 21/00
[52] U.S. Cl. .................................... 422/67; 422/63; 422/64; 422/65; 422/66; 422/105; 436/43; 436/44; 436/46; 436/48; 436/50; 436/55
[58] Field of Search ................ 422/65, 63, 64, 67, 422/66, 68.1, 105, 107, 108; 436/43, 44, 46, 47, 48, 50, 55

[56] References Cited

FOREIGN PATENT DOCUMENTS 0180792  5/1986  European Pat. Off. .
0416587  3/1991  European Pat. Off. .
0458138 11/1991  European Pat. Off. .
3717914 12/1987  Germany .
61-091571 5/1986  Japan .

OTHER PUBLICATIONS

Garrison, et al. "Pneumatic Touch Sensor" IBM Tech. Disclosure Bulletin, vol. 16 No. 6, Nov. 1973, pp. 2037–2040.

Primary Examiner—James C. Housel
Assistant Examiner—Long V. Le
Attorney, Agent, or Firm—Bardehle, Pagenberg, Dost, Altenburg, Frohwitter, Geissler and Partner

[57] ABSTRACT

A liquid sample automatic analyzer is achieved in which if any test strip is not placed at a photometric position for such a reason that a test strip automatic supply device has failed to supply the test strip, this failure is detected to enable automatic judgment on that the measured results of examination correspond to which samples. A presence/absence detector is provided in the test strip automatic supply device, and a pressure detector for detecting whether the test strip is gripped or not is provided in a grip device. Detection signals from the presence/absence detector and the pressure detector are supplied to a control unit. Based on those detection signals, the control unit determines a failure in taking out or gripping the test strip, if occurs. Accordingly, even when the test strip is not placed at the photometric position in the measuring device and a vacant position occurs, this occurrence of the vacant position is detected to enable the analyzer to automatically and correctly judge that the measured results of examination correspond to which samples.

6 Claims, 8 Drawing Sheets

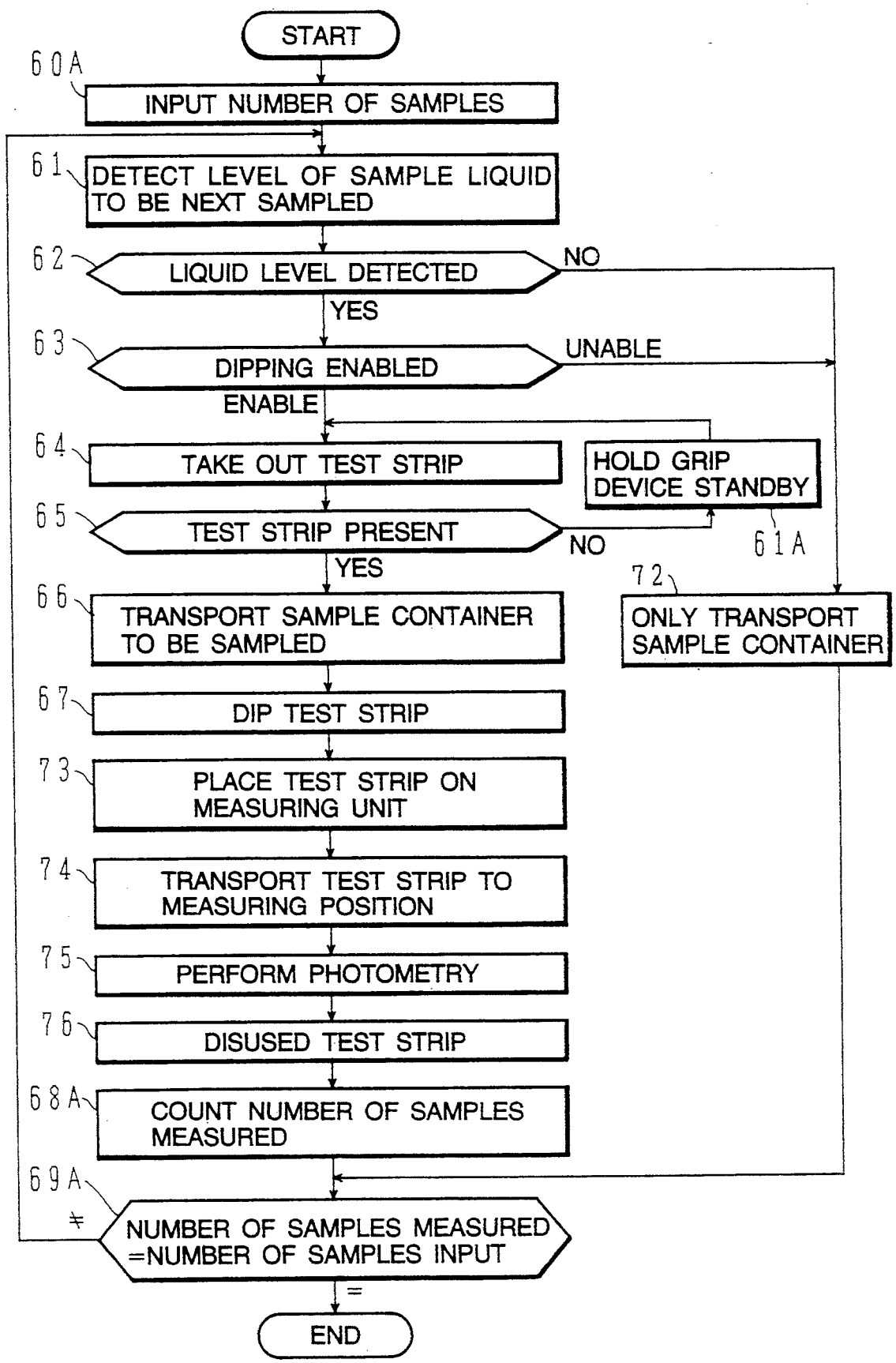

LIQUID SAMPLE AUTOMATIC ANALYZER

BACKGROUND OF THE INVENTION

The present invention relates to a liquid sample automatic analyzer for dipping a test strip in a liquid sample, such as urine and blood, to develop a color reaction for analysis of the sample.

Biochemistry components such as protein, glucose, ketone and occult blood in urine or pH of the urine, etc. are importantly concerned with health of human bodies, and are essential items to be measured in clinical examination. Methods of analyzing those items are divided into an quantitative analysis using reagents added to liquid sample in test tubes to develop reactions therein, and a semi-quantitative analysis using color reaction test strips. The latter analyzing method has been widely used in screening test for a group examination or diagnosis of diseases, because analysis results on many items can be readily and quickly obtained. The test strip consists of a plastic strip and reagent layers adhered to the plastic strip. The reagent layers are felts impregnate with reagent. The test strip is dipped into the urine in the test tube, being lifted from the test tube. The color tones of the reagent layers are observed by an operator to analyze the liquid sample when a predetermined time elapsed after the test strip was lifted from the test tube.

Urine examination using such color reaction test strips is primarily performed by operators visually checking the developed color tones. Recently, however, a demand for automatic urine analysis and hence a need for automatic analyzers in which all analyzing steps are automated have been increased for the reasons of an increase in the number of samples to be examined in examination rooms, a short of hands, and reluctance to those works handling urine. Adopting those automatic analyzers is effective in accurately controlling the time required to keep the test strips dipping in urine and controlling the elapse time required from lifting of test strips to measuring of the test strip. Further, the automatic analyzer can prevent errors due to individual differences in determining coloration of the test strip. Therefore, reliability of the examined results can be improved. There is thus a tendency that the automatic analyzers will be more and more widespread in future.

At present, liquid sample automatic analyzers are divided into two types; i.e., the dipping type that a test strip is inserted and dipped into a sample liquid in a sample container, and the pipetting type that a sample is sucked by a nozzle and discharged in a predetermined amount onto reagent layers on the surface of a test strip to be checked. The pipetting type analyzer has disadvantages of requiring a pump adapted to pipet the sample liquid and increasing the analyzer size. Another disadvantage of the pipetting type analyzer is that because measurement accuracy would be affected if the surplus sample is left on the test strip after dropping the sample and making it permeate into the test strip. Therefore, an additional work of removing the surplus sample is required, which renders the analyzing operation more complicated. On the other hand, the dipping type analyzer in which a test strip is dipped into a sample liquid is automated directly following the analyzing steps which are manually carried out in usual cases. This enables measurement to be performed with simple mechanisms and good reproducibility.

As one example of analyzers for automatically dipping test strips into sample liquids, an automatic analyzer is disclosed in JP, A, 61-91571 (JP, B, 4-26434).

The automatic analyzer disclosed in JP, A, 61-91571 comprises a test strip automatic supply mechanism including presence/absence and upper/lower surface detecting means, a sample container supply mechanism for automatically supplying sample containers in which liquid samples are contained, a liquid level detecting mechanism for detecting a liquid level in each sample container and, by way of example, informing a shortage of the liquid to be examined, and a photometric mechanism for making photometry on the test strips having been dipped in the samples. The disclosed automatic analyzer also comprises a test strip automatic handling mechanism for taking out each test strip from the test strip automatic supply mechanism, dipping it into the sample liquid in the sample container, and moving the test strip to the photometric mechanism after the dipping, and a control unit for controlling the operation of the test strip automatic supply mechanism and so forth.

By using the disclosed liquid sample automatic analyzer, labor imposed on the operators is reduced and reproducibility of measurement is improved.

SUMMARY OF THE INVENTION

In the above liquid sample automatic analyzer of prior art, although the steps of dipping test strips into samples and making photometry on the test strips having been dipped are automated, judgment on that the measured results of examination correspond to which samples must be made by the operator. Therefore, when a test strip holder or the like has failed to hold any test strip, this failure cannot be detected and the photometric operation is successively continued for subsequent test strips in the liquid sample automatic analyzer of prior art. Accordingly, there is a possibility that any sample may be regarded as having been examined in spite of the same sample having been not actually examined, and the relationship between the liquid samples and the examined results may become unclear.

It is an object of the present invention is to realize a liquid sample automatic analyzer in which if any test strip is not placed at a photometric position for such a reason that a test strip automatic supply device has failed to supply the test strip, this failure is detected to enable automatic judgment on that the measured results of examination correspond to which samples.

To achieve the above object, the present invention is constituted as follows.

A liquid sample automatic analyzer of the present invention comprises a test strip automatic supply device including containing means for containing a plurality of test strips, moving means for moving the test strips from said containing means to a test strip supply position one by one, and test strip detecting means for detecting whether the test strip is moved to said test strip supply position; a sample shifting device capable of arranging thereon a plurality of sample containers each containing a liquid sample, and shifting said plurality of sample containers to a test strip dipping position one by one; a measuring device including test strip carrying means for carrying the test strip from a predetermined initial position to a photometric position, and photometric means for performing photometry on the test strip placed at said photometric position, test strip handling device, provided with a grip device, for gripping the test strip set at the test strip supply position in said test strip automatic supply device, moving the gripped test strip to the test strip dipping position in said sample shifting device, dipping the gripped test strip into the liquid sample, and setting the dipped test strip at the initial position in said measuring device, and control/processing unit for controlling operation of said test strip automatic supply device, said sample shifting device, said measuring device and said test strip handling device, executing a predetermined data processing on measured data of the test strip from said photometric means to make analysis, and determining the case where the test strip is not placed at the photometric position in said measuring device, based on a detection signal from said test strip detecting means in said test strip automatic supply device, so that said predetermined data processing is to be executed only on the measured data resulted when the test strip is placed at said photometric position.

In the above liquid sample automatic analyzer, preferably, said grip device includes grip detecting means for detecting whether the test strip is gripped or not, and said control/processing unit determines the case where the test strip is not placed at the photometric position in said measuring device, based on the detection signal from said test strip detecting means and a detection signal from said grip detecting means, so that said predetermined data processing is to be executed only on the measured data resulted when the test strip is placed at said photometric position.

In the above liquid sample automatic analyzer, preferably, said test strip detecting means is an optical reflection type detector comprising a light emitting element and a light receiving element.

Also, a liquid sample automatic analyzer of the present invention comprises a test strip automatic supply device including containing means for containing a plurality of test strips, and moving means for moving the test strips from said containing means to a test strip supply position one by one; a sample shifting device capable of arranging thereon a plurality of sample containers each containing a liquid sample, and shifting said plurality of sample containers to a test strip dipping position one by one; a measuring device including test strip carrying means for carrying the test strip from a predetermined initial position to a photometric position, and photometric means for performing photometry on the test strip placed at said photometric position; test strip handling device, provided with a grip device and grip detecting means for detecting whether the test strip is gripped or not by said grip device, for gripping the test strip set at the test strip supply position in said test strip automatic supply device, moving the gripped test strip to the test strip dipping position in said sample shifting device, dipping the gripped test strip into the liquid sample, and setting the dipped test strip at the initial position in said measuring device; and control/processing unit for controlling operation of said test strip automatic supply device, said sample shifting device, said measuring device and said test strip handling device, executing a predetermined data processing on measured data of the test strip from said photometric means to make analysis, and determining the case where the test strip is not placed at the photometric position in said measuring device, based on a detection signal from said grip detecting means, so that said predetermined data processing is to be executed only on the measured data resulted when the test strip is placed at said photometric position.

Preferably, the above liquid sample automatic analyzer further comprises liquid amount detecting means for detecting the amount of liquid sample in each of said sample containers arranged on said sample shifting device, wherein said control/processing unit determines whether the liquid amount is enough for making measurement or not, based on a detection signal from said liquid amount detecting means, so that said predetermined data processing is to be executed only on the measured data resulted when the test strip having been dipped into the liquid sample of measurable amount is placed at said photometric position.

In the above liquid sample automatic analyzer, preferably, said control/processing unit ceases the operation of said test strip automatic supply device, said sample shifting device, said measuring device and said test strip handling device when said liquid amount detecting means detects two times in succession that the liquid sample is not present in said sample container.

In the above liquid sample automatic analyzer, preferably, said control/processing unit includes input means for entering the number of samples to be measured, compares the number of samples entered from said input means with the number of data supplied from said photometric means, and ceases the operation of said test strip automatic supply device, said sample shifting device, said measuring device and said test strip handling device when the number of samples entered agrees with the number of data supplied.

In the above liquid sample automatic analyzer, preferably, said test strip carrying means carries the test strip intermittently from the predetermined initial position to the photometric position.

Furthermore, in the above liquid sample automatic analyzer, preferably, said grip detecting means is a pressure detector, and said control/processing unit determines whether the test strip is gripped or not, based on a difference between the grip pressure detected when the test strip is gripped by said grip device and the pressure detected when the test strip is not gripped.

In the liquid sample automatic analyzer of the present invention, a plurality of sample containers each containing a liquid sample are arranged on the sample shifting device and shifted to the test strip dipping position successively. The test strip automatic supply device transports a plurality of test strips to the test strip supply position one by one. The test strip handling device grips the test strip placed at the test strip supply position, dips it into the liquid sample in the sample container at the test strip dipping position, and then sets the dipped test strip at the test strip initial position in the measuring device. In the measuring device, the test strip set at the test strip initial position is carried to the photometric position where the test strip is measured. When the test strip is not taken out due to bending or tangling thereof and no test strip is supplied from the test strip automatic supply device, the control/processing unit determines that the test strip is not placed at the photometric position in the measuring device, and executes the predetermined data processing only on the measured data resulted when the test strip is placed at the photometric position.

BRIEF DESCRIPTION OF THE DRAWINGS

FIG. 10 is a flowchart showing the operation of a second embodiment of the present invention.

DETAILED DESCRIPTION OF THE PREFERRED EMBODIMENTS

A first embodiment of the present invention will be described with reference to the attached drawings. In this first embodiment, the present invention is applied to a urine automatic analyzer.

Figure 1:
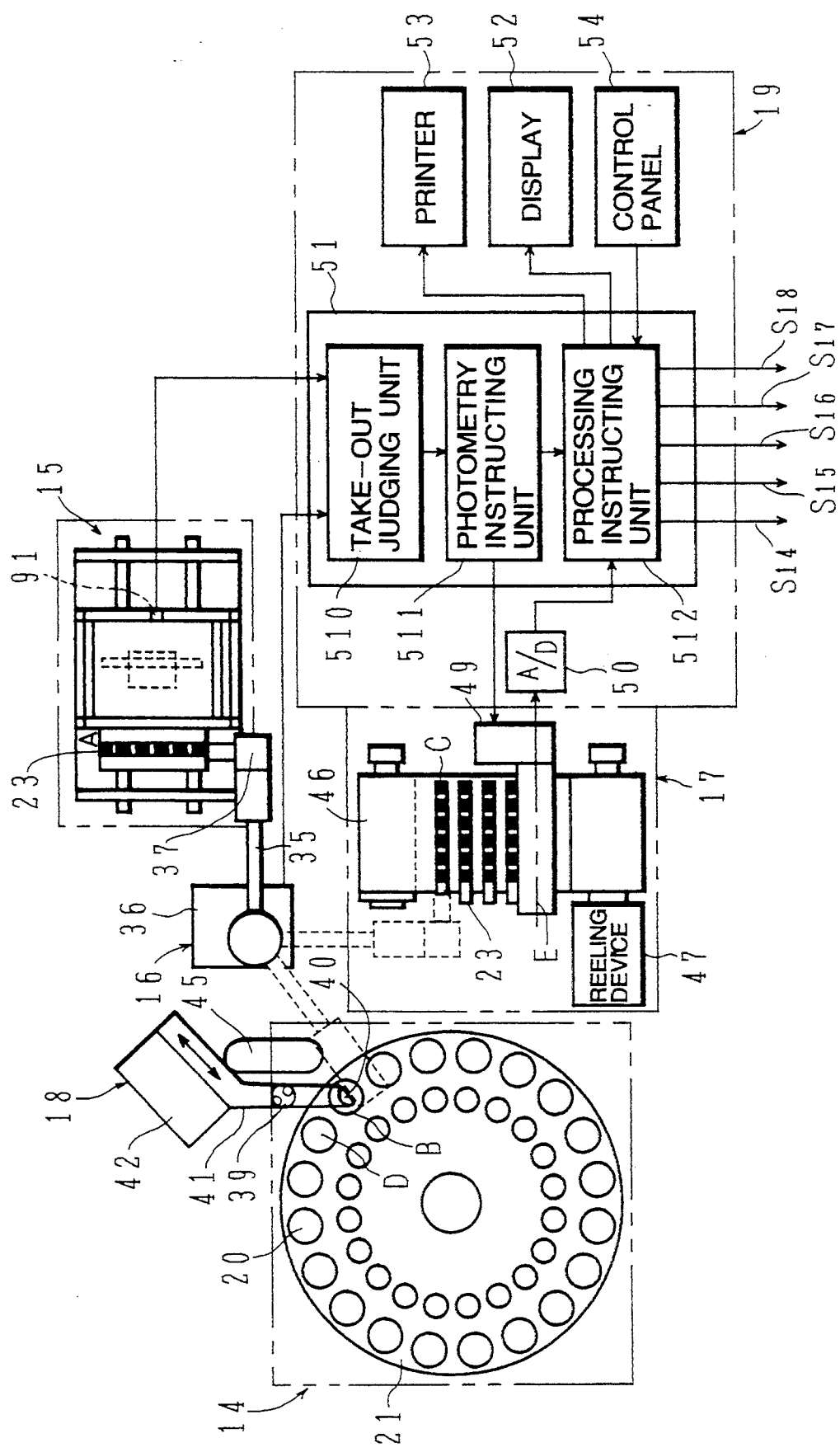
FIG. 1 is a view showing the general schematic configuration of a first embodiment of the present invention.

FIG. 1 is a view showing the general schematic configuration of the first embodiment. In FIG. 1, the urine automatic analyzer comprises a sample shifting device(-turntable) 14, a test strip automatic supply device 15, a test strip handling device 16, a measuring device 17, a sample liquid amount detecting device 18, and a control/processing unit 19. The control/processing unit 19 controls the operation of the sample shifting device 14, the test strip automatic supply device 15, the test strip handling device 16, the measuring device 17, and the sample liquid amount detecting device 18. More specifically, the control/processing unit 19 includes a control unit 51 which comprises a take-out judging unit 510, a photometry instructing unit 511, and a processing instruction unit 512. Control signals S14 and S15 are supplied from the processing instructing unit 512 to the sample shifting device 14 and the test strip automatic supply device 15, respectively. Also, control signals S16, S17 and S18 are supplied from the processing instructing unit 512 to the test strip handling device 16, the measuring device 17, and the sample liquid amount detecting device 18, respectively.

The sample shifting device 14 includes a turntable 21 on which a number of sample containers 20 each containing a urine sample to be analyzed are arranged along a circle. The turntable 21 is intermittently rotated with predetermined time intervals for shifting the sample containers 20 to a test strip dipping position B successively. The number of sample containers 20 capable of being loaded on the turntable 21 is sixty in this embodiment (though only twenty sample containers are shown for brevity).

Figure 2A:
FIGS. 2A and 2B are explanatory views of a test strip for use in the first embodiment of the present invention.
Figure 2B:

The test strip automatic supply device 15 has a function of supplying test strips 23 stored therein beforehand one by one in synchronism with the analyzing cycle. Each of the test strips 23 used in this embodiment has a number of reagent layers 25 which are linearly arranged on the strip surface, as shown in FIGS. 2A and 2B. Total eleven reagent layers 25 are provided corresponding to ten analysis items plus one for color correction. The total length of the test strip 23 is about 120 mm, and the length of an area in which the reagent layers 25 are arranged is about 90 mm. In order to make the entire reagent layers sufficiently dipped, therefore, a sample liquid in the sample container is required to have a liquid level not lower than 90 mm. Sample containers generally used for urine analysis have a length of about 100 mm.

Figure 3:
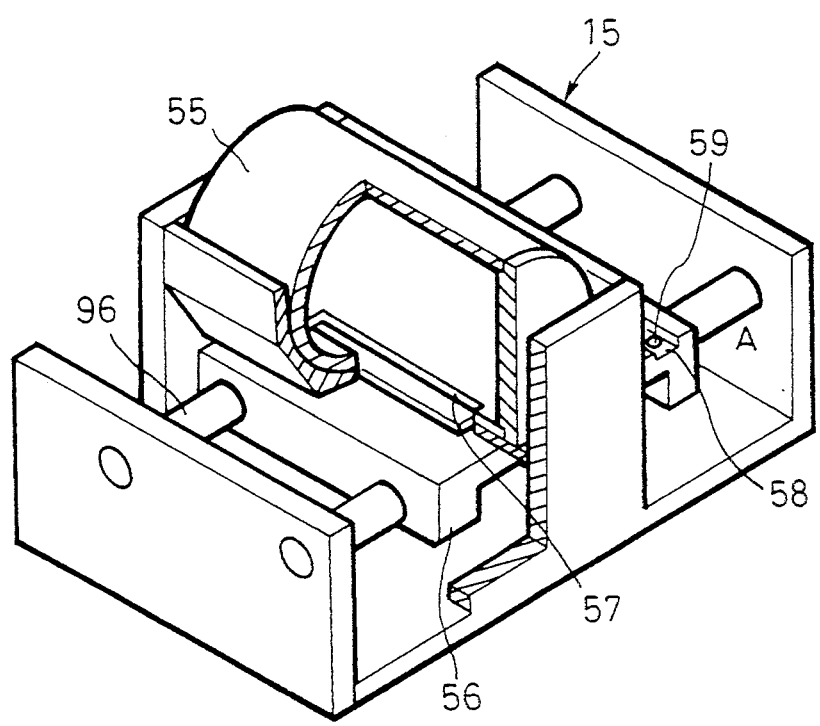
FIG. 3 is a schematic perspective view of a test strip automatic supply device.
Figure 4:
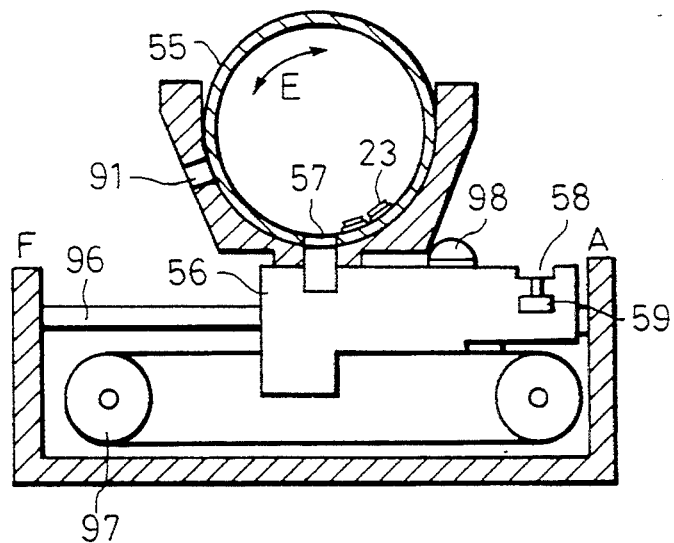
FIG. 4 is a schematic sectional view of the test strip automatic supply device.

FIG. 3 is a schematic perspective view, partly broken, of the test strip automatic supply device 15, and FIG. 4 is a schematic sectional view of the supply device 15.

In FIGS. 3 and 4, the test strip automatic supply device 15 includes a tubular container body (test strip containing means) 55 capable of containing a plurality of test strips 23. The container body 55 is constructed so as to reciprocally turn in directions as indicated by E in FIG. 4. A slit 57 extending parallel to an axis of rotation of the container body 55 is formed through an inner peripheral wall of the container body 55. The slit 57 is sized and shaped to be able to receive the test strip 23. When the container body 55, including the slit 57, is reciprocally rotated, one test strip 23 is held in the slit 57. Whether the test strip 23 is held in the slit 57 or not is detected by a test strip presence/absence detector (test strip detecting means) 91 disposed in an outer peripheral wall of the container body 55. The test strip 23 held in the slit 57 is then received by a receiving groove 58 formed in a test strip transporting stage (moving means) 56.

When receiving the test strip 23, the test strip transporting stage 56 is moved by a drive motor 97 along stage support shafts 96 to a position indicated by F in FIG. 4 so that the test strip 23 is received by the receiving groove 58 now moved to position just below the slit 57. After the test strip 23 has been received by the receiving groove 58, a upper/lower surface detector 59 disposed in the receiving groove 58 detects whether the test strip 23 faces up properly or not (i.e., the side of the test strip 23 on which the reagent layers 25 are not pasted (the back side) lies to face the detector 59 or not). If the test strip 23 does not face up properly, the test strip 23 is reversed by a test strip reversing mechanism 98. After that, the test strip 23 held by the receiving groove 58 is moved by the test strip transporting stage 56 to a test strip taking-out position indicated by A in FIG. 4. Incidentally, the drive motor 97 is omitted in FIG. 3.

The presence/absence detector 91 and the upper/lower surface detector 59 are each a small-sized reflection type detector comprising a light emitting element (e.g., an LED) for emitting a light of particular wavelength and a light receiving element (e.g., a photodiode). Also, the test strip 23 has a black mark so as to enable discrimination on which side is the front surface. The presence/absence detector 91 detects a white area of the test strip 23 by emitting the light to the white area from the light emitting element and receiving the light reflected therefrom by the light receiving element. The upper/lower surface detector 59 is adjusted in its location and sensitivity so that the black mark on the test strip 23 can be detected by emitting the light to the black mark from the light emitting element and receiving the light reflected therefrom by the light receiving element. Upon detecting the test strip, the presence/absence detector 91 supplies a signal indicating the presence of the test strip to the take-out judging unit 510 of the control unit 51.

While the presence/absence detector 91 is disposed in the outer peripheral wall of the container body 55 in this embodiment shown in FIG. 4, it may be disposed in the receiving groove 58 in parallel to the upper/lower surface detector 59.

Referring back to FIG. 1, the test strip handling device 16 includes a drive mechanism 36 for enabling an arm 35 to move vertically and turn horizontally, and a test strip grip device 37 provided at a distal end of the arm 35 to be capable of gripping the test strip and turning about its axis. The test strip handling device 16 functions to grip the test strip 23 placed at the test strip supply position A in the test strip supply device 15, dipping it into the sample liquid in the sample container 20 placed at the dipping position B, lifting the test strip 23 out of the sample liquid after a predetermined period of time, moving it to a test strip set position (initial position) C on the measuring device 17, followed by releasing the test strip 23 from its gripped state.

Figure 5:
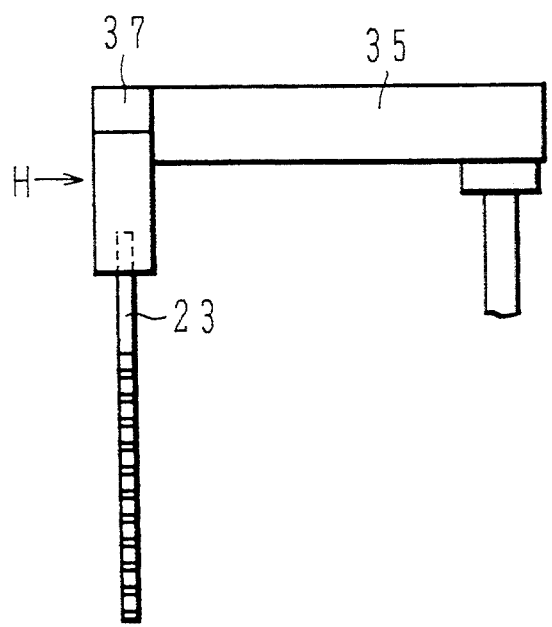
FIG. 5 is an enlarged view of a grip device.
Figure 6:
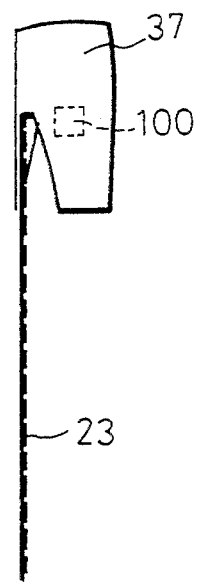
FIG. 6 is a side view of the grip device as viewed in a direction of H shown in FIG. 5.

FIG. 5 is an enlarged view of the grip device 37 of the test strip handling device 16, and FIG. 6 is a schematic side view of the grip device 37 as viewed in a direction of H in FIG. 5. The grip device 37 includes a pressure detector 100. The pressure detector 100 is constituted to be able to detect whether the grip device 37 has gripped the test strip 23 or not. The reason why the arm 35 and the grip device 37 shown in FIG. 5 are different in shape from those shown in FIG. 1 is that the two parts in FIG. 1 are illustrated in the simplified form. Under a condition where the pressure detector 100 is gripping the test strip 23, a signal indicating that the test strip is held in a gripped state is supplied from the handling device 16 to the take-out judging device 510 of the control unit 51.

Referring to FIG. 1 again, the sample liquid amount detecting device 18 includes an arm 41 which is provided with a level detecting electrode 39. The level detecting electrode 39 comprises a pair of rod-shaped electrodes extending toward the sample shifting device 14. The arm 41 is horizontally movable by a drive mechanism 42 in directions of arrows in FIG. 1. The arm 41 is also vertically movable by the drive mechanism 42.

The level of the sample liquid in the sample container 20 is detected as follows. First, the electrode 39 is moved and inserted into the sample container 20 locating at a liquid level detecting position D which is one step before the dipping position B. It is then determined by the control/processing unit 19 whether the level or amount of the sample liquid exceeds a minimum necessary value or not. The level or amount of the sample liquid is calculated from the distance through which the electrode 39 has moved downwardly until reaching the liquid level.

One rod-shaped electrode of the level detecting electrode 39 has its distal end curved into the scoop-like form to double as a stirrer. For the sample to be subjected to the subsequent analysis, the stirrer is moved up and down several times by operating the arm 41 to reciprocate vertically, whereby the sample liquid is stirred and mixed uniformly. Thereafter, the sample container 20 at the liquid level detecting position D is shifted to the dipping position B. Under this condition, the test strip 23 is carried by the test strip handling device 16 to the dipping position B where the grip device 37 descends the test strip 23 while gripping it, so that the test strip 23 is dipped into the sample container 20 at the dipping position. After the dipping for a predetermined period of time, the grip device 37 is ascended to lift the test strip 23 out of the sample liquid, following which the test strip 23 is carried to the test strip set position C on the measuring device 17. At this time, the test strip 23 on which color reactions have begun to develop is released from the grip device 37. Then, the arm 41 is horizontally moved to a washing tank 45 and the electrode 39 is descended into the washing tank 45. The electrode 39 descended into the washing tank 45 is washed by a washing liquid and, thereafter, it is ascended to be ready for the level detection of the next sample. Additionally, a distal end 40 of the arm 41 has a rod-shaped portion further extending from the electrode 39 toward the sample shifting device 14. When the amount of sample liquid in the sample container 20 at the dipping position B is a little smaller than the minimum necessary value, the rod-shaped portion is inserted in the sample container 20 to raise the liquid level.

Figure 7:
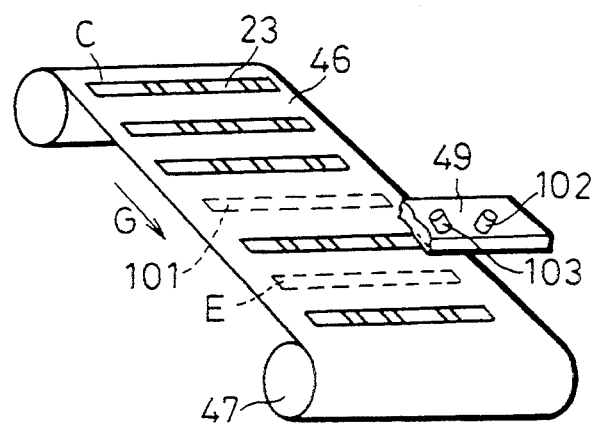
FIG. 7 is an enlarged schematic perspective view of a measuring device.

In the measuring device 17, the test strip 23 under color reactions received at the position C from the test strip handling device 16 is intermittently moved with a rolled paper 46 in a direction of arrow G shown in FIG. 7. More specifically, at the time the grip device 37 sets the test strip 23 in the position C, the paper 46 is held stopped. After the grip device 37 has released the test strip 23, the paper 46 is moved through the distance corresponding to a space between the test strips set adjacently on the paper 46, while the grip device 37 is moved away from the measuring device 17, passes the test strip automatic supply device 15 and the sample shifting device 14, and then comes back to the measuring device 17 again.

The rolled paper 46 is reeled up by the reeling device 47 with predetermined time intervals to intermittently move the test strip 23 as mentioned above. A photometer 49 is disposed at the position corresponding to a photometric position E, and includes a plurality of small-sized reflection type detectors each of which comprises a light emitting element 102 for emitting a light of particular wave-length corresponding to one of analysis items and a light receiving element 103. These reflection type detectors are arranged in one-to-one relation to the reagent layers on the test strip 23 for measuring the intensity of lights reflected from the respective reagent layers where reaction colors have already developed. The measured results are supplied to the control unit 51 through an A/D converter 50 and, after being subjected to data processing, they are indicated on a liquid crystal display 52 and also printed out by a printer 53. The analyzing operation by this analyzer proceeds upon entry from a control panel 54. Thus, an operator depresses keys or buttons on the control panel 54 for supplying necessary information to the processing instructing unit 512. Then, the operator depresses a start button on the control panel 54 for starting the measurement. The test strip 23 having measured is reeled up by the reeling device 47 into a roll along with the paper 46. After the measurement, the test strips 23 and the rolled paper 46 are removed and disused together.

Since the reeling device 47 reels up the rolled paper 46 with the predetermined time intervals as mentioned above, there occurs a vacant position 101 (see FIG. 7) in a row of the test strips 23 if any test strip is not supplied. A failure in supply of the test strip 23 is caused, for example, when the grip device 37 has failed to grip the test strip 23. Such a failure can be detected by the take-out-out judging unit 510 in advance based on the signals supplied from the presence/absence detector 91 and the pressure detector 100 of the grip device 37. Then, when the take-out judging unit 510 determines that the test strip 23 could not be properly taken out or gripped, a signal indicating this determination is supplied to the photometry instructing unit 511. Upon receiving that determination signal, the photometry instructing unit 511 supplies a control signal to the photometer 49 for controlling it so that the photometric operation will not be carried out when the vacant position 101 reaches the photometric position E. Simultaneously, the photometry instructing unit 511 also supplies the processing instructing unit 512 with a signal indicating that the photometric operation is temporarily suspended. Upon receiving that signal, the processing instructing unit 512 supplies control signals to the test strip automatic supply device 15 and the test strip handling device 16 for causing these devices to respectively take out and grip the test strip once again.

Figure 8:
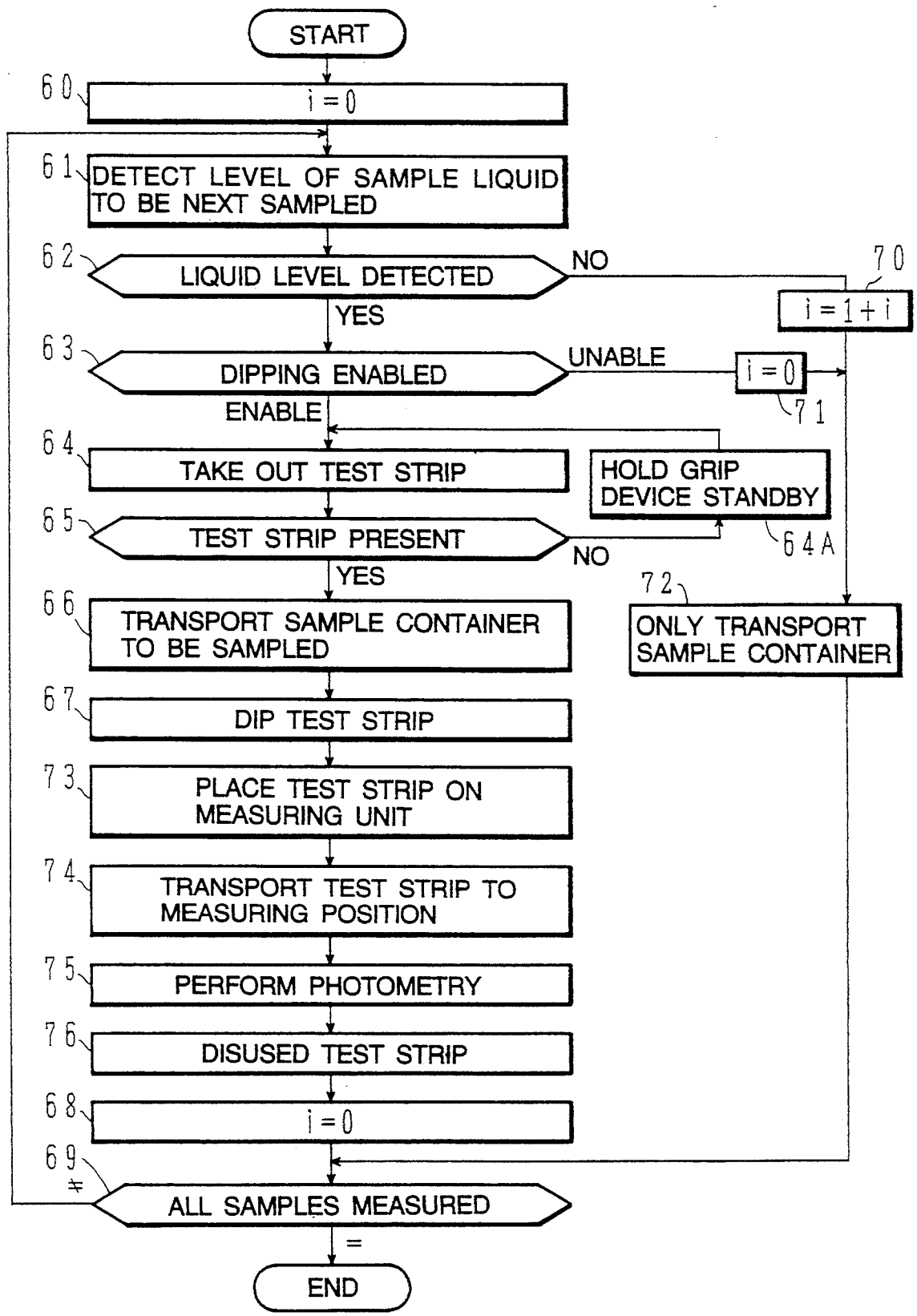
FIG. 8 is a flowchart showing the operation of the first embodiment shown in FIG. 1.

FIG. 8 is a flowchart showing the operation of the first embodiment explained above.

In step 60 of FIG. 8, information i for determining whether all the samples have been measured or not is initialized to 0 by the control unit 51. In step 61, the level of the sample liquid in the sample container 20 to be next sampled or measured is detected by the sample liquid amount detecting unit 18. It is determined in step 62 whether the liquid level has been detected or not. If the liquid level has not been detected, then the process flow goes to step 70 where i is incremented by one. Thereafter, the process flow goes to step 72 where the sample container 20 is shifted to the next position by the sample shifting device 14. In this case, the test strip 23 is not dipped into the sample. Subsequently, the process flow goes to step 69 for determining whether i is 2 or not. If i is 2, then the process is ended and, if i is not 2, then it returns back to step 61.

Figure 9:
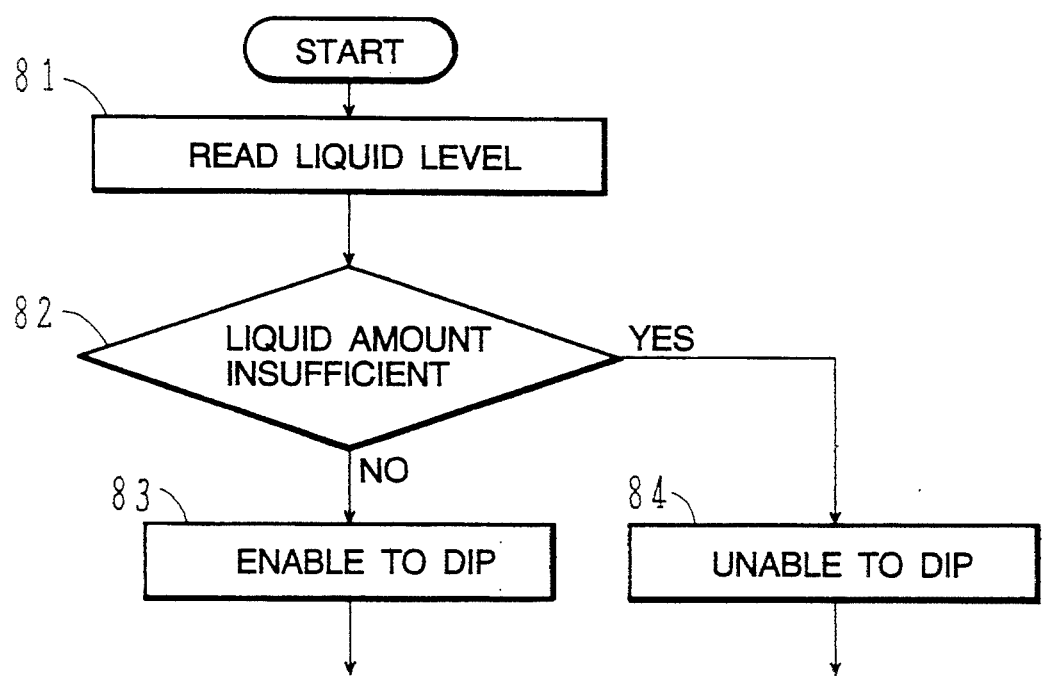
FIG. 9 is a flowchart for explaining step 63 shown in FIG. 8 in detail.

If the liquid level has been detected in step 62, then the process flow goes to step 63 for determining whether the liquid amount is enough for making the test strip 23 dipped therein. Details of step 63 is shown in FIG. 9. First, in step 81, the sample level in the sample container 20 is read. It is then determined in step 82 whether the liquid amount is sufficient or not. If the liquid amount is insufficient, then step 84 determines that it is unable to dip the test strip. If the liquid amount is sufficient, then step 83 determines that it is able to dip the test strip. If it is unable to dip the test strip, then the process flow goes from step 63 in FIG. 8 to step 71 where the information i for determining whether all the samples have been measured or not is set to 0. In this case, the control unit 51 stores the number of the sample into which the test strip could not be dipped, and also increments the sample count by one. For the sample into which the test strip could not be dipped, the sample number and the fact of incapability to dip are displayed on the display 52, for example. Afterward, the process flow goes from step 71 to step 72 where the sample container 20 is shifted to the next position by the sample shifting device 14, followed by going to step 69.

If it is able to dip the test strip in step 63, then the process flow goes from step 64. In step 64, the test strip is taken out by the test strip automatic supply device 15 and the test strip handling device 16. In next step 65, the take-out judging unit 510 determines whether the grip device has failed to grip the test strip or not. If the taking-out of the test strip has failed, then it is determined that the test strip is absent, followed by returning via step 64A to step 64 where the operation of taking out the test strip is carried out once again. When taking out the test strip once again, this is properly adjusted in timing with the operation of the grip device 37 and the operation of the reeling device 47. More specifically, the grip device 37 is held standby in step 64A for a period of time required in a normal cycle for the grip device 37 to take out the test strip, moves away from the automatic supply device 15 and then comes back to the automatic supply device 15 via the sample shifting device 14 and the measuring device 17. After holding the grip device 37 standby for the above required time in step 64A, the process flow returns to step 64.

As mentioned above, when the operation of taking out the test strip has failed, the vacant position 101 occurs in the measuring device 17. However, because the vacant position 101 is detected and known to the control unit 51, the photometer 49 is controlled not to make photometry for the vacant position 101 at the time the vacant position 101 reaches the photometric position E.

If the test strip is determined to be present in step 65, then the process flow goes step 66 where the sample container to be measured is shifted to the dipping position B. In step 67, the test strip 23 gripped by the grip device 37 is dipped into the sample. Subsequently, the process flow goes step 73 where the test strip 23 is lifted out of the sample by the grip device 37 and set on the paper 46 in the measuring device 17. The test strip 23 set on the paper 46 is moved to the photometric position E in step 74, and is subjected to photometry by the photometer 49 in step 75. A set of data resulted from the photometry is supplied to the processing instructing unit 512 of the control unit 51 via the A/D converter 50.

The processing instructing unit 512 processes the data supplied thereto and also counts the number of data sets. On this occasion, the processing instructing unit 512 can correctly count the number of data sets because even if the vacant position 101 occurs, this is known to the unit 512, as explained above.

In next step 76, the test strip 23 on which the photometry has been completed is disused into a predetermined container (not shown) or the like. Thereafter, the process flow goes to step 68 where the information i is initialized to 0, followed by going to step 69 to determine whether i is 2 or not. If i is 2, then the sampling or analyzing operation is ended.

Thus, the sampling operation is ended when the liquid level is not detected two times in succession. This step can be realized by arranging the plurality of sample containers 20, each containing the sample liquid, on the turntable 21 one after the other and removing two or more sample containers from the positions subsequent to the last sample container 20 containing the sample.

With the first embodiment of the present invention, as described above, it is arranged such that a failure in taking out or gripping the test strip 23 can be known to the control unit 51 by disposing the presence/absence detector 91 in the test strip automatic supply device 15 and also disposing the pressure detector 100, which detects whether the test strip has been gripped or not, in the grip device 37. With this arrangement, at the time the vacant position 101 where the test strip 23 is absent reaches the photometric position E, the photometer is controlled not to make the photometry. Accordingly, a urine automatic analyzer is achieved which can automatically and correctly judge that the measured results of examination correspond to which samples.

Further, with the first embodiment, it is arranged such that whether the test strip can be dipped into the sample liquid in the sample container 20 or not is detected by the sample liquid amount detecting device 18 and if the test strip cannot be dipped, the number of the relevant sample and the fact of incapability to dip are indicated by the control/processing unit 19. Accordingly, the sample of which amount is insufficient for analyzing it can be correctly detected and management of the analyzed samples is facilitated.

The above first embodiment is arranged to judge that all the samples have been measured, when the liquid level is not detected two times in succession. As an alternative, however, such a judgment may be effected by entering the total number of samples to the processing instructing unit 512 from the control panel 54 in advance, and comparing the entered number and the counted number of samples having been measured.

FIG. 10 is a flowchart showing the operation of a second embodiment of the present invention. In this embodiment, the number of samples to be measured is entered in advance. Note that the general construction of the second embodiment is similar to that of the first embodiment and, therefore, is not illustrated. A sample shifting device, a test strip automatic supply device, a test strip handling device, a measuring device, a sample liquid amount detecting device, etc. are similar to those of the first embodiment and, therefore, are not illustrated. Further, steps 61 to 67 and 72 to 76 in the operation flowchart for this embodiment shown in FIG. 10 are similar to the steps 61 to 67 and 72 to 76 shown in FIG. 8.

In step 60A shown in FIG. 10, the number of samples to be measured is entered from a control panel similar to the control panel 54 shown in FIG. 1 and stored in storage means within the processing instructing unit 512. After that, the steps 61 to 67 and the steps 73 to 76 are executed, following which the process flow goes from step 76 to step 68A. However, if the liquid level is not detected in step 62, then the process flow goes to step 68A via step 72. Further, if it is determined in step 63 that the test strip cannot be dipped into the sample, then the process flow also goes to step 68A via step 72.

In step 68A, the number of samples having been measured is counted. Subsequently, in step 69A, the counted number of samples is compared with the number of samples input and stored in step 60A. If the counted sample number is not equal to the stored sample number, then the process flow returns to step 61. If the counted sample number is equal to the stored sample number in step 69A, then the process is completed and the sampling operation is brought into an end.

With the second embodiment as described above, similarly to the first embodiment, a urine automatic analyzer is achieved which can automatically and correctly judge that the measured results of examination correspond to which samples. Further, with the second embodiment, the number of samples is stored in advance and the sampling operation is automatically ended when the samples in the same number as the stored number have been examined. Accordingly, the time elapsed from the start of examination to the end thereof can be shorter than that required in the first embodiment.

As a modification, a means for detecting the occurrence of the vacant position where the test strip 23 is absent may be disposed near the photometer 49 in the measuring device 17 shown in FIG. 4, an output signal of the detecting means being supplied to the control unit 51.

While the above first and second embodiments are in connection with urine automatic analyzers, the present invention is not limited to urine automatic analyzers, but can also be applied to automatic analyzers, intended for other liquid samples, using test strips.

While the rolled paper 46 is reeled up to move intermittently, it may be continuously moved at a low speed rather than intermittently.

Also, the above first and second embodiments are arranged such that when the vacant position 101 occurs and reaches the photometric position E, the photometer 49 is controlled not operate. However, it may be arranged such that the photometer 49 is operated for the vacant position 101 as well, but the processing instructing unit 51 does not handle the resulted data as effective data.

Moreover, the above first and second embodiments are arranged such that the occurrence of the vacant position 101 is detected based on both the detection signals from two detecting means; i.e., the presence/absence detector 91 and the pressure detector 100. But the occurrence of the vacant position 101 may be detected based on only the detection signal from the presence/absence detector 91. Alternatively, it may be detected based on only the detection signal from the pressure detector 100.

The present invention constructed as set forth above has the following advantages.

The liquid sample automatic analyzer of the present invention comprises a test strip automatic supply device including means for containing a plurality of test strips, means for moving the test strips from the containing means to a test strip supply position one by one, and means for detecting whether the test strip is moved to the test strip supply position; a sample shifting device for shifting a plurality of sample containers to a test strip dipping position one by one; a measuring device including means for carrying the test strip from an initial position to a photometric position, and means for performing photometry on the test strip; test strip handling device for gripping the test strip, moving it to the test strip dipping position, dipping it into the liquid sample, and setting the dipped test strip at the initial position in the measuring device; and control/processing unit for controlling operation of the test strip automatic supply device, the sample shifting device, the measuring device and the test strip handling device, executing a predetermined data processing on measured data of the test strip from the photometric means to make analysis, and determining the case where the test strip is not placed at the photometric position, based on a detection signal from the test strip detecting means, so that the predetermined data processing is to be executed only on the measured data resulted when the test strip is placed at the photometric position. Accordingly, the liquid sample automatic analyzer is achieved in which even when the test strip is not placed at the photometric position for such a reason that the test strip automatic supply device has failed to supply the test strip, this is detected to enable the analyzer to automatically and correctly judge that the measured results of examination correspond to which samples.

Alternatively, the liquid sample automatic analyzer of the present invention comprises a test strip automatic supply device including means for containing a plurality of test strips and means for moving the test strips from the containing means to a test strip supply position one by one; a sample shifting device capable of arranging thereon a plurality of sample containers each containing a liquid sample, and shifting the plurality of sample containers to a test strip dipping position one by one; a measuring device including means for carrying the test strip from a predetermined initial position to a photometric position, and means for performing photometry on the test strip placed at the photometric position; test strip handling device, provided with a grip device and means for detecting whether the test strip is gripped or not by the grip device, for gripping the test strip set at the test strip supply position in the test strip automatic supply device, moving it to the test strip dipping position in the sample shifting device, dipping it into the liquid sample, and setting the dipped test strip at the initial position in the measuring device; and control/processing unit for controlling operation of the test strip automatic supply device, the sample shifting device, the measuring device and the test strip handling device, executing a predetermined data processing on measured data of the test strip from the photometric means to make analysis, and determining the case where the test strip is not placed at the photometric position in the measuring device, based on a detection signal from the grip detecting means, so that the predetermined data processing is to be executed only on the measured data resulted when the test strip is placed at the photometric position. Accordingly, the liquid sample automatic analyzer is achieved in which even when the test strip is not placed at the photometric position for such a reason that the grip device has failed to grip the test strip, this is detected to enable the analyzer to automatically and correctly judge that the measured results of examination correspond to which samples.

What is claimed is:

1. A liquid sample automatic analyzer comprising:
   a test strip automatic supply device including containing means for containing a plurality of test strips, and moving means for moving the test strips from said containing means to a test strip supply position one by one; a sample shifting means for shifting a plurality of sample containers, each containing a liquid sample, to a test strip dipping position one by one;
   a measuring device including test strip carrying means for carrying the test strip from a predetermined initial position to a photometric position and photometric means for performing photometry on the test strip placed at said photometric position;
   a test strip handling device, provided with a grip device and grip detecting means for detecting whether the test strip is gripped or not by said grip device, for gripping the test strip set at the test strip supply position in said test strip automatic supply device, moving the gripped test strip to the test strip dipping position in said sample shifting means, dipping the gripped test strip into the liquid sample, and setting the dipped test strip at the initial position in said measuring device; and
   a control/processing unit for controlling operation of said test strip automatic supply device, said sample shifting device, executing a predetermined data processing on measured data of the test strip from said photometric means to make analysis, and determining the case where the test strip is not placed at the photometric position in said measuring device, based on a detection signal from said grip detecting means, so that said predetermined data processing is to be executed only on the measured data resulted when the test strip is placed at said photometric position.

2. A liquid sample automatic analyzer according to claim 1, further comprising liquid amount detecting means for detecting an amount of liquid sample in each of said sample containers arranged on said sample shifting means, wherein said control/processing unit determines whether the liquid amount is enough for making measurement or not, based on a detection signal from said liquid amount detecting means, so that said predetermined data processing is to be executed only on the measured data resulted when the test strip having been dipped into the liquid sample of measurable amount is placed at said photometric position.

3. A liquid sample automatic analyzer according to claim 2, wherein said control/processing unit ceases the operation of said test strip automatic supply device, said sample shifting device, said measuring device and said test strip handling device when said liquid amount detecting means detects two times in succession that the liquid sample is not present in said sample container.

4. A liquid sample automatic analyzer according to claim 1 or 2, wherein said control/processing unit includes input means for entering a number of samples to be measured, compares the number of samples entered from said input means with a number of data supplied from said photometric means, and ceases the operation of said test strip automatic supply device, said sample shifting device, said measuring device and said test strip handling device when the number of samples entered agrees with the number of data supplied.

5. A liquid sample automatic analyzer according to claim 1, wherein said test strip carrying means carries the test strip intermittently from the predetermined initial position to the photometric position.

6. A liquid sample automatic analyzer according to claim 1, wherein said grip detecting means is a pressure detector, and said control/processing unit determines whether the test strip is gripped or not, based on a difference between a grip pressure detected when the test strip is gripped by said grip device and a pressure detected when the test strip is not gripped.

* * * * *

UNITED STATES PATENT AND TRADEMARK OFFICE
CERTIFICATE OF CORRECTION

PATENT NO. : 5,415,840
DATED : May 16, 1995
INVENTOR(S) : Kazuhiro Sano, Susumu Kai, Shigeru Yonekawa It is certified that error appears in the above-indentified patent and that said Letters Patent is hereby corrected as shown below:

```
Col. 1,  ln. 38, replace "works" with --workers--;
Col. 1,  ln. 47, insert --the-- between "in" and "future";
Col. 2,  ln. 42, delete "is" which appears between "invention"
    and "to";
Col. 5,  ln. 63, replace "Total eleven" with --A total of eleven--;
Col. 8,  ln. 57, replace "disused" with --discarded--;
Col. 9,  ln. 39, replace "is" with --are--;
Col. 9,  ln. 60, replace "from" with --to--;
Col. 10, ln. 6,  replace "moves" with --moved--;
Col. 10, ln. 7,  replace "comes" with --brought--;
Col. 10, ln. 21, replace "goes step" with --goes to step--;
Col. 10, ln. 25, replace "goes step" with --goes to step--;
Col. 10, ln. 30, replace "resulted" with --resulting--;
Col. 10, ln. 41, replace "disused" with --discarded--;
Col. 10, ln. 67, replace "that the" with --which--;
Col. 11, ln. 52, replace "into" with --to--;
Col. 11, ln. 54, replace "similarly" with --similar--;
```

UNITED STATES PATENT AND TRADEMARK OFFICE
CERTIFICATE OF CORRECTION

PATENT NO. : 5,415,840
DATED : May 16, 1995
INVENTOR(S) : Kazuhiro Sano, Susumu Kai, Shigeru Yonekawa It is certified that error appears in the above-indentified patent and that said Letters Patent is hereby corrected as shown below:

```
Col. 11, ln. 56, replace "that the" with --which--;
Col. 12, ln. 14, replace "not operate" with --not to operate--;
Col. 12, ln. 63, replace "that the" with --which--.
```

Signed and Sealed this

Seventeenth Day of October, 1995

Attest:

BRUCE LEHMAN

*Attesting Officer*   *Commissioner of Patents and Trademarks*